United States Patent [19]
Richter et al.

[11] Patent Number: 5,312,624
[45] Date of Patent: * May 17, 1994

[54] DRAIN TREATMENT PRODUCT AND METHOD OF USE

[75] Inventors: Francis L. Richter, Circle Pines; James Wilson, Maplewood; Daniel E. Pedersen, Cottage Grove, all of Minn.

[73] Assignee: Ecolab Inc., St. Paul, Minn.

[*] Notice: The portion of the term of this patent subsequent to May 28, 2008 has been disclaimed.

[21] Appl. No.: 51,580

[22] Filed: Apr. 22, 1993

Related U.S. Application Data

[60] Continuation of Ser. No. 661,697, Feb. 27, 1991, abandoned, which is a division of Ser. No. 247,279, Sep. 21, 1988, Pat. No. 5,019,346.

[51] Int. Cl.$^5$ .................... A01N 25/08; C11D 17/00
[52] U.S. Cl. .................... 424/405; 4/222; 4/223; 4/227.1; 4/231; 252/106; 252/134; 252/DIG. 16; 424/408; 424/409
[58] Field of Search ........... 4/222, 223, 227.1, 231; 252/106, 134, DIG. 16; 424/405, 408, 409

[56] References Cited

U.S. PATENT DOCUMENTS

| | | | |
|---|---|---|---|
| 2,087,592 | 7/1937 | Chesnut | 252/156 |
| 3,112,499 | 12/1963 | Thornton | 4/222 |
| 3,597,772 | 8/1971 | Leavitt et al. | 4/222 |
| 3,721,629 | 3/1973 | Goodenough | 252/106 X |
| 3,724,002 | 4/1973 | Buck, Jr. | 4/222 |
| 3,856,932 | 12/1974 | May | 424/405 |
| 4,119,578 | 10/1978 | Daeninckx et al. | 252/548 |
| 4,218,432 | 8/1980 | Watanabe et al. | 424/405 |
| 4,224,701 | 9/1980 | Huang | 4/679 |
| 4,269,723 | 5/1981 | Barford et al. | 252/106 |
| 4,308,625 | 1/1982 | Kitko | 4/227.6 |
| 4,318,193 | 3/1982 | Bayer et al. | 4/222 |
| 4,460,490 | 7/1984 | Barford et al. | 252/92 |
| 4,536,367 | 8/1985 | Hung et al. | 4/227.1 X |
| 4,574,403 | 3/1986 | Dintemann et al. | 4/309 |
| 4,578,207 | 3/1986 | Holdt et al. | 252/134 |
| 4,624,713 | 11/1986 | Morganson et al. | 134/25.2 |
| 4,683,072 | 7/1987 | Holdt et al. | 252/102 |
| 4,738,728 | 4/1988 | Barford et al. | 4/227.1 X |
| 4,820,449 | 4/1989 | Menke et al. | 252/DIG. 16 X |
| 4,861,511 | 8/1989 | Kaplan | 252/174.23 |
| 4,911,859 | 3/1990 | Bunczk et al. | 252/106 |

OTHER PUBLICATIONS

M. Doyle, Annual Review of Nutrition 5, 25 (1985).
Official Methods of Analysis of the Association of Official Analytical Chemists, edited by Sidney Williams (14th Ed. 1984), Sections 4.020–4.029.
Pesticide Assessment Guidelines, Subdivision G: Product Performance for the United States Environmental Protection Agency, (Nov.–82) (Doc. No. PB83-153924).
Cosmetic Ingredient Dictionary, 150, 174, 175, 203, 299, 300 (Third Ed. 1982).
The Condensed Chemical Dictionary 567 (10th Ed. 1981).
Material Safety Data Sheet, Union Carbide Corporation, Aug. 31, 1981.

(List continued on next page.)

*Primary Examiner*—Thurman K. Page
*Assistant Examiner*—Robert H. Harrison
*Attorney, Agent, or Firm*—Merchant, Gould, Smith, Edell, Welter & Schmidt

[57] ABSTRACT

A drain sanitizing article (9) for reducing microbiological activity in drain runoff areas having a housing (10), the housing having an inner wall (16) defining an inner opening (18) in the housing, an outer wall (12), and a bottom wall (14) defining a central cavity (15) in the housing (10), a tear strip (20) for destructibly removing the housing outer wall and a portion of the bottom wall (14), a handle (30) spanning the inner opening (18) of the housing (10) and joined to the inner wall (16) of said housing (10); and a chemical sanitizing agent (40).

52 Claims, 3 Drawing Sheets

OTHER PUBLICATIONS

Morton Thiokol, Inc. Material Safety Data Sheet.
Material Safety Data Sheet on Perox Red 32.
Material Safety Data Sheet, Union Carbide Corporation, Mar. 11, 1981.
Shell Chemical Company Technical Bulletin–SC:1-31-82.
FMC technical information.
Industrial Uses of ACL Chlorinating Compositions, Monsanto Corporation.
Germicidal Quaternaries, Group II–Cationics, Onyx Chemicals (now Stepan Chemical Company).
Physical Properties of Dowicide Products, Dow Chemical Company.
Technical information on Shell's NEODOL product line.
Technical information on BASF Wyandotte's PLURONIC product line.
GAF Chemicals Corporation Table II physical data on Igepal CO surfactants.
Articles, Blow Molding, Injection Molding, and Thermoforming, Wiley Encyclopedia of Packaging Technology, 54, 406, 668 (1986).

DRAIN TREATMENT PRODUCT AND METHOD OF USE

This is a continuation of application Ser. No. 661,697, filed Feb. 27, 1991, which was abandoned upon the filing hereof, which is a division of application Ser. No. 07/247,279, filed Sep. 21, 1988, U.S. Pat. No. 5,019,346.

FIELD OF THE INVENTION

The present invention relates generally to drain sanitizing articles and more particularly to an improved drain sanitizing article for food processing and preparation environments which will provide prolonged sanitizing in floor drains.

DESCRIPTION OF THE PRIOR ART

The troublesome reoccurrence of food born diseases caused by psychrotrophic, pathogenic micro-organisms has created strong concern within the food process industry and has fueled a search for new environmental sanitation products targeted at these micro-organisms. Public awareness of food born diseases has dramatically increased recently due to the occurrence of epidemics of both listeriosis and salmonellosis.

Between Jan. 1 and Jun. 14, 1985, 86 cases of *Listeria monocytogenes* infection were diagnosed in the area of Orange County, and Los Angeles, Calif. with 29 deaths resulting from ingestion of contaminated mexican-style cheese. This outbreak followed an earlier 1983 occurrence of 49 diagnosed cases of listeriosis in Massachusetts between Jun. 30 and Aug. 30 with 14 deaths caused by consumption of milk. Between Mar. 22 and Apr. 6, 1985, 5,770 culture-confirmed cases of salmonellosis were reported to the Illinois Department of Public Health caused by an outbreak of milk born *Salmonella tychimurium*. This was the largest number of confirmed salmonellosis cases ever associated with a single outbreak in the United States.

The symptoms of these diseases can manifest a number of different forms. In neonatal infants, the disease often can be characterized by symptoms of sepsis or meningitis. In pregnant women, the disease often takes the form of a puerperal sepsis or non-specific flu-like illness which can result in the premature delivery of stillborn or acutely ill infants. Doyle, M. P.; *Food Borne Pathogens of Recent Concern;* Ann. Rev. Nutr. 1985; Vol. 5, pages 25–41.

The FDA has responded to these recent outbreaks of listeriosis and salmonellosis with expanded plant audits and new test protocols to isolate pathogens in those areas which foster microbiological contaminants. The FDA designed one such procedure for drains, the logic being that pathogens present in the general plant environment would eventually find their way into the drain where growth may occur. In accord with the FDA's renewed focus on this area of the plant environment, there now exists a renewed need for an active continuous drain sanitizer in the food process environment.

SUMMARY OF THE INVENTION

The drain sanitizing article of this invention is a solid drain treatment product designed to sanitize, control odors, clean soil, and control biofilm build-up in drains, troughs, and pits. The drain sanitizing article of this invention is also designed to be effective in environments such as overhead drip and collection pans, or any plant or processing area where water flow causes a general environmental sanitation concern in the dairy and food process industries.

The present invention comprises a sanitizing article for reducing microbiological activity in drain run off areas, including a housing having an inner wall, defining an inner opening in the housing, and an outer wall, the inner and outer walls being joined by a bottom wall and which altogether define an inner cavity for containing an active chemical sanitizing agent in the housing; a tear strip for destructibly removing the outer wall as well as a portion of the bottom wall of the housing, the tear strip being wholly incorporated into the outer wall of the housing; a handle spanning the inner opening of the housing and joined to the inner wall of the housing; and a active sanitizing agent which fills the inner void within the housing.

The sanitizing article of the present invention is intended to be a solid developed for continuous controlled release of active sanitizing agents. The sanitizing article of the present invention includes an active sanitizing agent as well as a housing. The housing functions as a mold for the formation of the active sanitizing agent, a container for safely and continually holding the active sanitizing ingredient during storage as well as application, and a dispenser facilitating in-drain placement. Finally, the invention is intended to provide rapid visual evidence of placement, and dissolution of the active sanitizing agent from within the housing.

DETAILED DESCRIPTION OF THE INVENTION

Figure 1:
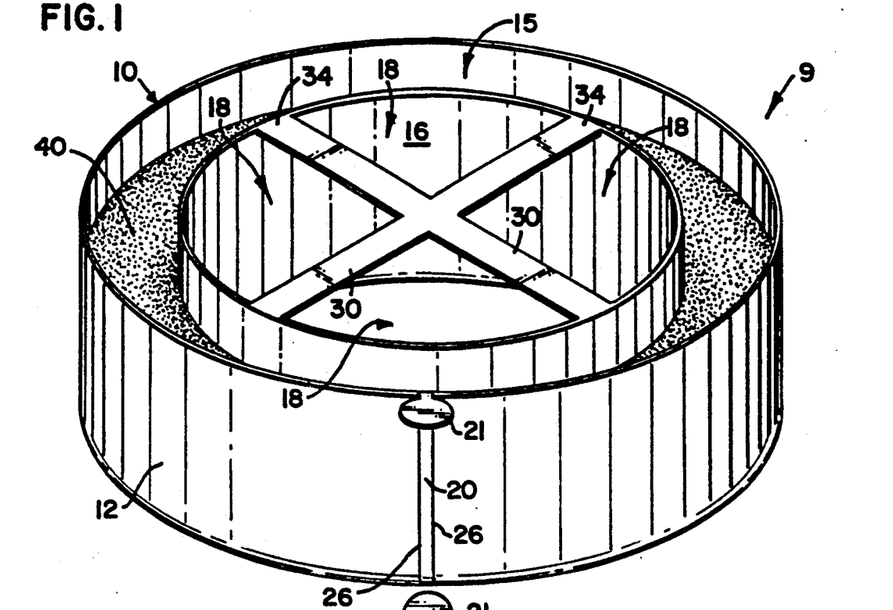
FIG. 1 is a perspective view of the drain sanitizing article in accordance with one embodiment of the present invention.
Figure 2:
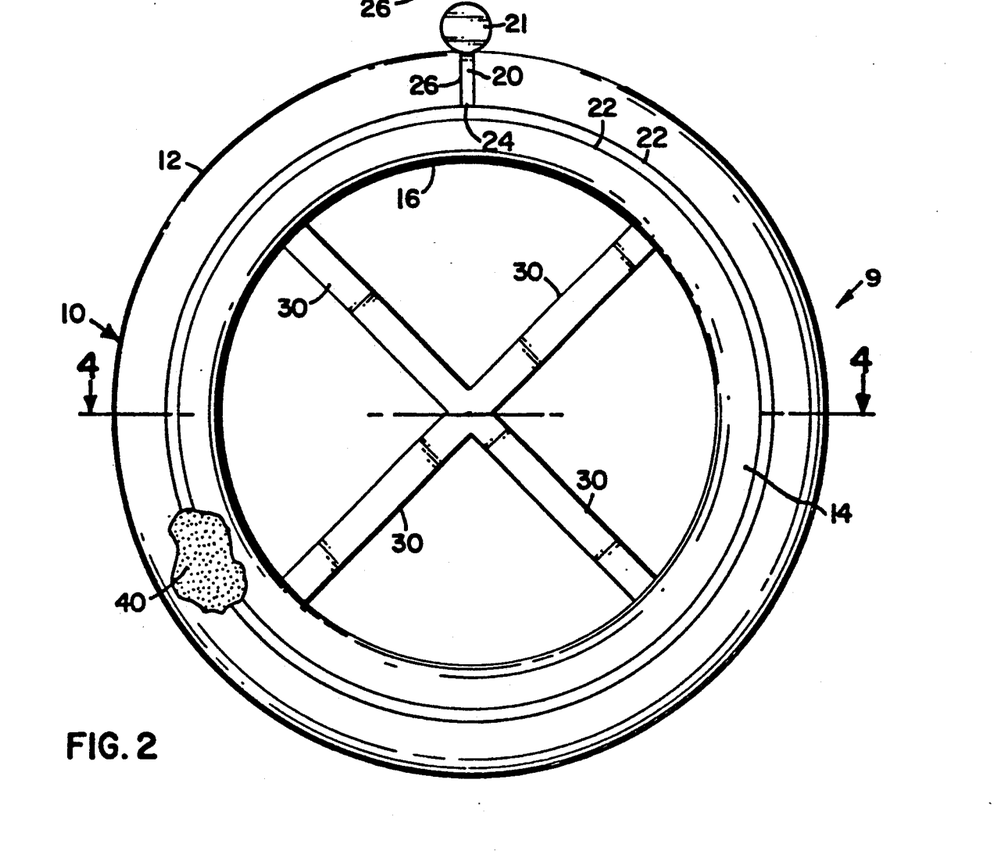
FIG. 2 is a bottom plan view of the drain sanitizing article shown in FIG. 1.

Referring to the drawings wherein like numerals represent like parts throughout the several views, there is generally shown a drain sanitizing article (9). Generally, the drain sanitizing article (9) comprises a housing (10) containing a chemical sanitizer (40). As shown in FIG. 1, the housing (10) has an inner wall (16), an outer wall (12), the inner and outer walls being cooperatively connected by a bottom wall (14). The inner wall (16) defines an inner opening (18) in the housing (10). As shown in FIG. 2, the inner wall (16), the outer wall (12), and the bottom wall (14) define a cavity within the housing (10) of the sanitizing article (9). As shown in FIGS. 1 and 2, the inner opening (18) of the housing (10) is partially obstructed by a handle (30). The handle (30) is cooperatively connected to the inner wall (16) of the housing (10) at joint (34).

Figure 3:
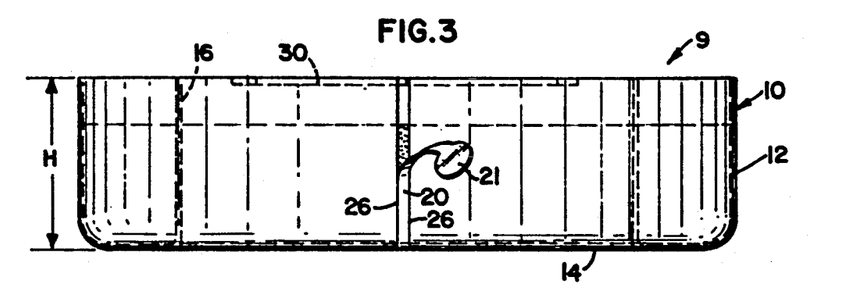
FIG. 3 is a side view of the drain sanitizing article shown in FIG. 1 showing a preferred feature of the tear strip means for destructibly removing portion of the housing of the present invention. As depicted, the tear strip is partially removed exposing the sanitizing agent.

As shown in FIG. 3, a tab (21) is affixed to a tear strip (20) which is defined as the area between the coarsed lines (26). The tear strip (20) facilitates the removal of a portion of the housing (10) which, as shown, includes the outer wall (12) and a portion of the outer perimeter of the bottom wall (14). The tear strip (20) joins perimeter coarsed or molded lines (22) at an abuttment point (24), FIG. 2. The perimeter coarsed lines (22) allow complete removal of the intended portion of the housing (10) once the tear strip (20) is used to break the outer wall (12) of the housing (10).

Generally, the housing (10) of the drain sanitizing article (9) should retain a composition, shape and size which facilitates effective application and placement in drain areas in food process environments. Specifically, the housing (10) functions as a mold in the transformation of the chemical sanitizer (40) to hardened form. The housing (10) also serves as a manufacturing, shipping, and storage container preventing premature contamination of the chemical sanitizer (40) prior to use. Finally, the housing (10) serves as a dispenser when the chemical sanitizer (40), now in hardened form, is placed in the intended environment of application.

The sanitizing article may be placed into the intended application of use encased as manufactured, or, alternatively, with a portion of the housing (10) destructibly removed by the tear strip (20). Finally, it is within the scope of this invention that the chemical sanitizer (40), once hardened, can be removed altogether from the housing (10) by destructibly removing the intended portion of the housing (10) through the tear strip (20). Once partially exposed, the hardened chemical sanitizer (40) is merely removed by flexing the housing (10) and placed within the drain.

Commensurate with the intended use of the sanitizing article of this invention, the housing (10) should be tolerant to the processing temperatures of the chemical sanitizing agent (40). Also, the housing (10) must be made of a material which retains a certain degree of flexibility thereby allowing placement of the drain sanitizing article (9) in drains which are not of complementary shape and size and allowing flexure of the housing (10) to assist in the complete removal of the chemical sanitizer (40).

Generally, any plastic polymeric material or mixtures of polymers which will provide all of these requisite functions will be suitable. Specifically, polyethylene and polypropylene of an appropriate thickness have been found preferable in forming the housing (10) of the present sanitizing article. Polyethylene provides processing ease and is readily amenable to being molded into a one-piece housing (10), handle (30), and tear strip (20). On the other hand, polypropylene has a high temperature tolerance and thus can withstand the processing temperatures and extended cooling times incumbent in the formation of a solid chemical sanitizer (40).

The contrasting considerations of providing a tear strip which enables removal of a portion of the housing (10) and providing a housing (10) having a high temperature tolerance present a very difficult engineering problem. Generally, polypropylene and high density polyethylene provide excellent high temperature tolerance but preclude the formation of a viable tear strip. The alternative is fabricating the housing from a polyethylene or a mixture of polypropylene and polyethylene or a mixture of other polymers having the appropriate density.

The polymer used for forming the housing (10) may also be capable of imparting a translucent character or accepting pigments to provide a colored or shaded housing (10), once molded. A dyed chemical sanitizer (40), in combination the translucent housing (10), or a dyed or shaded housing (10) in combination with the chemical sanitizer (40), allows the operator to easily choose the correct drain sanitizing article (9) from the storage shelf merely by visually recognizing the appropriate color. In such an instance, the individual operator need not resort to a detailed consideration the parameters affecting use of the drain sanitizing article for each of possibly hundreds of drains in the plant such as drain flow, temperature of drainage, intended environment of application, or the specific food processing which is being undertaken at the location of the drain. This may be done initially and then merely followed by the simple replacement of a drain sanitizing article having the same color. Moreover, a translucent housing (10) in combination with a dyed chemical sanitizer or, alternatively, a colored housing (10) in combination with an unpigmented chemical sanitizer (40), allows visual recognition that drain sanitizing article (9) has exhausted the entirety of the chemical sanitizer (40) and must be replaced.

The housing (10) is preferably polymeric and thus may be formed by any processes commonly available and known within the plastics molding art. Generally, processes such as injection molding, blow molding, thermo or vacuum forming, or the like, may be used to form the housing (10). Preferably, the housing (10), tear strip (20), and handle (30) will be molded or formed as one piece with a minimal amount of secondary processing. Injection molding provides a cost conservative process which is not limited either by the amount of trimming which must be done once the housing (10) is formed or limited by a number of features which are intended to be used with the housing (10). For instance, the integral inclusion of a tear away strip (20) is difficult to provide for when vacuum forming or thermoforming processes are used. A detailed discussion of the variety of processes which can be used to mold the housing of the present invention is available in the *Wiley Encyclopedia of Packaging Technology*, 1986, edited by M. Bakker, and published by Wiley Press, New York, N.Y. which is incorporated herein by reference.

Moreover, the thickness of the housing (10) is readily variable to provide for application of the sanitizing article in differing environments when the housing is molded by injection processes. Generally, the thickness of the housing will vary within a range intended to provide a housing strong enough to withstand the fill temperature of the chemical sanitizing agent while still providing a enough flexibility to be collapsed for removal the chemical sanitizer (40), once hardened. The thickness of the polymeric housing will range from about 0.020 inches to 0.060 inches with a more preferred range being from about 0.030 inches to 0.050 inches and most preferably about 0.040 inches.

Regarding the shape and size of the sanitizing article, the majority of drains within the food processing industry measure in diameter from 4 inches to 2 feet. Most drains, regardless of their size at the floor level, funnel down to a 4 inch drain pipe. Indeed, a rough survey of the drains most often found in the food processing industry discloses a size range of approximately 6 to 12 inches in diameter. With this in mind, the drain sanitizing article should be shaped and sized to facilitate manufacture, and, most importantly, proper application within the intended environment of use.

Preferably, the outer diameter of the housing (10) is between 6–7 inches as this size has been found to most compatible with drains found in the food processing industry. More specifically, an outer diameter of 6.75 inches and an inner opening of approximately 4.75 inches allows the drain sanitizing article (9) to be placed in run-off areas where the housing handle (30) rests on a stand pipe (60) which projects into the actual area of the drain (50), FIG. 5.

Figure 4:
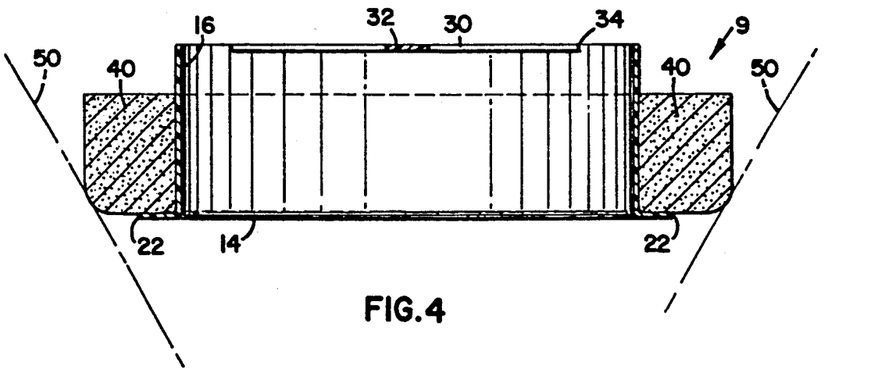
FIG. 4 is a cross-sectional view of the drain sanitizing article as shown in FIG. 2 taken along lines 4—4, with a portion of the housing removed exposing the chemical sanitizing agent.

The sanitizing article (9) is also intended to be capable of fitting shallower drains. The height, H, of the drain sanitizing article (9) must generally be kept to under 2 inches. Preferably, the height of the drain sanitizing article (9) is about 1.9 inches and most preferably the height is about 1.75 inches. Generally, with regard to shape, the sanitizing article, and more specifically, the housing (10) can take any shape which will fit within the intended drain. Preferably, the housing (10) is circular having in cross-section, an inner opening (18) which accommodates the funneling nature of most drains found in the industry (50). This structural shape also provides maximum contact between the chemical sanitizer (40) and drain run-off, FIG. 4, and allows for easier use of the tear strip (20) to remove the intended part of the housing (10).

The preferred embodiment of the present invention, provides a tear away strip (20), defined as the area between the coarsed lines (26) and optionally attached to a pull tab (21). This tear away strip functions to remove a portion of the housing (10) to expose the chemical sanitizer (40) which may include the outer wall (12) and a portion of the bottom wall (14). While the tear strip (20) may be used to remove only the outer wall (12) of the housing (10), the tear strip (20) preferably will serve to remove the outer wall (12) and a portion of the outer perimeter of the bottom wall (14).

Upon removal of the outer wall (12), the outer external surface of the chemical sanitizer (40) is additionally exposed to the flow of drainage. The exposure of the outer wall as well as the lower surface of the sanitizing prevents run-off from trickling down the drain walls (50) and underneath the normally encased sanitizing article (9), FIG. 4. Where the sanitizing article is placed in a conical funneling drain, the exposed chemical sanitizer (40) will rest against the narrowing sides of the drain (50). Drain run-off, coarsing down the sides of the drain (50) passes over the drain sanitizing article (9) and gradually dissolves the chemical sanitizer (40). As the chemical sanitizer (40) dissolves the drain sanitizing article (9) gradually moves down the sides of the drain maintaining contact with the drain wall (50). This positioning combined with the exposure of the chemical sanitizer (40) provides continued maximum surface area exposure to contact run-off over the life of the drain sanitizing article (9).

Moreover, the tear strip (20), enabling removal of a portion of the housing (10) allows the operator to dispense the chemical sanitizer (40) and completely remove it from the housing (10). Removal of the chemical sanitizer may be appropriate to obtain maximum sanitizing exposure when the sanitizing article (9) is intended to be used in an environment where the drainage flow is minimal.

Generally, the tear strip (20) may take any form which facilitates the removal of a portion of the housing (10). Preferably, the tear strip (20) allows removal of the housing outer wall (12) and the outer perimeter of the bottom wall (14) and is an integral part of a one-piece molded housing (10). As shown, the tear strip (20) is defined by weakened coarse or tear lines (26), (22) which are formed directly into the outer wall (12) and the bottom wall (14) of the housing (10) during the molding process. The use of such an embodiment facilitates the single piece molding of the housing (10) by modern blow, vacuum, and injection molding processes.

Preferably, the tear strip (20) is destructibly removed from the entire housing (10) at the abuttment point (24). The abuttment point (24) may be formed or defined on the outer wall (12) or bottom wall (14) of the housing (10) depending on the intended exposure to be given the chemical sanitizer (40). The abuttment point (24) may be a point where the tear strip separates from the housing (10). The outer wall (12) is thereby opened at the tear lines (26) and may be grasped and removed, FIG. 2, along with the appropriate section of the bottom wall (14), if desired, along the perimeter tear lines (22). Alternatively, the abuttment point (24) of the tear strip (20) may be a point where the tear strip (20) is integrally fused to the outer wall (12) or bottom wall (14), if desired, to be removed from the housing (10). Moreover, the tear strip (20) may be defined or patterned by coarse or tear lines (26) which angle towards the bottom of the housing (10) at less than 90°. An angled tear strip (20) which is integrally fixed to the housing (10) allows removal of the intended portion of the housing (10) and exposure of the chemical sanitizer (40) in one motion.

An additional aspect of the present- invention is a handle (30) which spans the inner opening (18) and is cooperatively connected to the housing (10) of the sanitizing article (9). If the chemical sanitizer (40) used is formulated through a heated mixing process, the handle (30) stabilizes the housing (10), preventing disfigurement while the chemical sanitizer (40) cools and hardens. The handle (30) assists in the placement and removal of a sanitizing article (9) within the drain. Also the handle (30) allows the sanitizing article to be easily removed from the drain during the cleaning of the floor and drain. This prevents undo waste of the chemical sanitizer (40) due to the excess run-off and drainage of wash water during such operations. For instance, in areas such as an industrial food product filling or packaging installation cleaning takes place daily. An inability to easily remove the sanitizing article (9) results in an unnecessary exposure of the article to excess drain run-off and drastically shortens the efficacious life span of the article (9).

The handle (30) may be cooperatively connected to the housing through any means known to those of skill in the art such as a snap attachment through a tongue and grove system, affixed by an adhesive or glue, thermally attached through the use of heat sensitive bonding agents, riveted to the housing (10), or the like. Preferably, the handle (30) is molded with the housing (10) as a one piece unit. Moreover, the handle (30) preferably retains the slight profile of the housing (10) represented by the height, H. The entire housing (10) maintains a low profile and, in turn, fits in shallower drains. In order to ensure the free flow of water through the inner opening (18) of the housing (10), the handle (30) preferably does not completely obstruct this inner opening (18).

Figure 5:
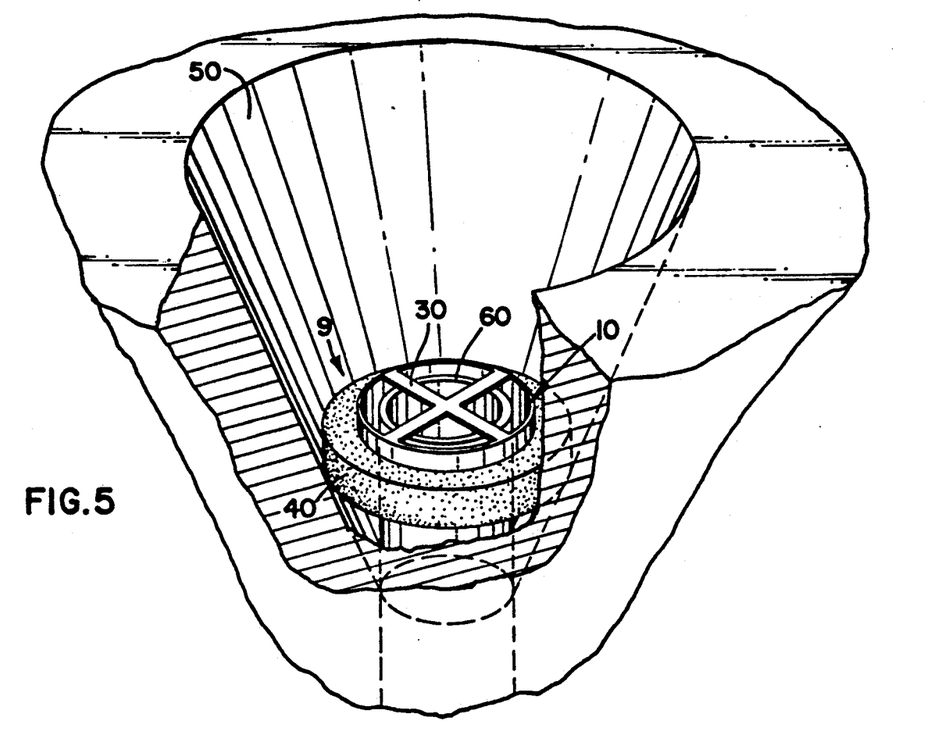
FIG. 5 is a perspective view of the drain sanitizing article shown in FIG. 1 placed within a drain environment.

In application environments having a standpipe protruding into the drain area, the handle (30) further allows placement and support of the sanitizing article housing (10) upon this standpipe, FIG. 5. The handle preferably spans the inner opening (18) of the housing to provide for placement of the sanitizing article (9) on the protruding standpipe. Given removal of the outer wall (12) and outer perimeter of the bottom wall (14) from the housing (10) such a configuration provides maximum water exposure to the chemical sanitizer (40).

With these requirements in mind, the handle (30) may generally take any form but preferably does not completely obstruct the inner opening (18) of the housing (10) to liquid flow, allows for the integral molding of the handle (30) to the housing (10), and ensures sturdy support of the housing (10) during placement, use, and removal of the drain sanitizing article (9) from the intended environment of application.

In accordance with another aspect of the present invention, there is provided a chemical sanitizer (40) which comprises a sanitizing agent, a hardener to stabilize and control solubility to the chemical sanitizer (40), and optionally a dye which when combined with the translucent polymeric housing provides a color indicative of the intended use environment the extent of use of the chemical sanitizer (40).

In the food processing industry, bacterial growth is dependent on many factors including the foods processed, the processing environment, including the temperature of the food processing facility as well as the frequency with which the facility is cleaned. Ultimately, bacteria is removed through cleaning processes which rely on disposal or drainage. Consequently, the drain area and any dead space therein presents a primary medium for the continued growth of microbes and bacterial contaminants which may lead to food born infectious diseases. By providing an active chemical cleaner which is capable of "sanitizing", the drain sanitizing article (9) of the present invention precludes the growth of all but the most insignificant amount of bacterial contaminants.

Accordingly, the sanitizing agent used in the chemical sanitizer (40) of the present invention preferably satisfies the definition of "sanitizer" as by the AOAC Official Methods of Analysis, *Germicidal and Detergent Sanitizing Action* §4.028 (1984). This AOAC use-dilution protocol is one of a small number of procedures generally recognized and professionally accepted for measuring biocidal activity. The sanitizing agent used in the chemical sanitizer (40) of the present invention should provide a "sanitizing" efficacy which will cause at least about 3 log count reduction or 99.9% in the number of organisms within 30 seconds to enable use within drains in food processing environments as required by EPA Guidelines for the food processing industry. The present chemical sanitizer is intended to ensure a continuous controlled release of the active sanitizing agents as well as detergents for the life of the drain sanitizing article. Moreover, the chemical sanitizer (40) of the present invention is intended to provide a certain degree of variability within its own chemical and physical properties. As a result, the drain sanitizing article (9) may be applied to any number of food processing environments while still providing effective sanitizing action once in place.

For example, the chemical sanitizer (40) of the present invention is intended to have the same level of efficacy in a cold water, low flow drain environment as in a hot water, high flow drain environment with the variance of certain constituents and the chemical sanitizer. Constant sanitizing efficacy is provided by varying the concentration and solubility of the sanitizing agent of the present invention.

The sanitizing agent may be one or more agents which function to provide the microbiocidal activity in the drain sanitizing article (9). Specifically, the sanitizing agent used should preferably fall within the well defined category of "sanitizers" having the capability to provide the necessary reduction in bacteria. Moreover, the chosen sanitizing agent may also function to deodorize the undesirable odors which often accompany microbial growth. Biofilm build up tends to result from the growth of bacteria within the drain region. Other soils such as milk soils and animal or vegetable processing by-products which also form in the drain region, in turn, result in bacterial growth. The formation of this residue creates a harboring environment for the sustained growth of more bacteria. Accordingly, the chemical used as the sanitizing agent is intended to function as a detergent assisting in the cleaning and removal of biofilms and other soils in the drain environment.

Generally, any solid or liquid chemical agent having a "sanitizing" level of bacteriocidal efficacy may be used as the sanitizing agent in the drain sanitizing article (9). Chemical compositions known to impart sanitizing efficacy include aldehydes, iodophors, phenolics, surfactants including anionic and cationic surfactants, and inorganic and organic chlorine releasing agents.

Representative compositions which could be used as the sanitizing agent of the present invention are commonly available aldehydes such as formaldehyde and glutaraldehyde; iodophors such as iodine-nonionic surfactant complexes, iodine-polyvinyl pyrollidone complexes, iodine-quaternary ammonium chloride complexes, and amphoteric iodine-amine oxide complexes and the like; organic chlorine releasing agents such as cyanurates, cyanuric acids, and dichlorocyanurate dihydrates which are commercially available from FMC and Monsanto as their CDB and ACL product lines, respectively; encapsulated or unencapsulated inorganic chlorine releasing agents such as alkalis and alkaline earth hypochlorites including NaOCl, KOCl, LiOCl, $Ca(OCl)_2$ and the like; fatty acids such as decanoic acid and the like; anionic surfactants such as dodecyl benzene sulfonic acid and sodium 1-octane sulfonate; phenols such as o-phenylphenol, 2,4,5-trichlorophenol, and 2,3,4,6-tetrachlorophenol commercially available from sources such as Dow Chemical Company and Mobay Chemical Company. Also found to be useful as the sanitizing agent within the chemical sanitizer (40) of the present invention are cationic surfactants including quaternary ammonium chloride surfactants such as n-alkyl($C_{12-18}$) dimethyl benzyl ammonium chloride, n-alkyl($C_{14-18}$) dimethyl benzyl ammonium chloride, n-tetradecyl dimethyl benzyl ammonium chloride monohydrate, n-alkyl($C_{12-14}$) dimethyl 1-naphthylmethyl ammonium chloride commercially available from manufacturers such as Stepan Chemical Company.

Preferably, the sanitizing agent is a cationic quaternary alkyl dimethyl benzyl ammonium chloride having an alkyl chain length which generally can range from about $C_8$ to $C_{18}$. Quats have been found to be most preferable due to their commercial availability and high sanitizing efficacy. These sanitizing agents are also preferred because of their compatibility to high water temperatures, the presence of high organic loads, stability in variable high and low pH wash systems and their non-corrosive nature. Preferably, the alkyl chain length of a quat will be from $C_{10}$ to about $C_{16}$ or mixtures. Preferably, the sanitizing agent used within the invention is a quaternary ammonium chloride conforming to the formula $[CH_3 (CH_2)_{13} N(CH_3)_2 CH_2 C_6H_5]Cl^-$ which in essence has a mixture of n-alkyl chain lengths including 60 wt. % $C_{14}$, 30 wt. % $C_{16}$, 5 wt. % $C_{12}$, and 5 wt. % $C_{18}$ and is commercially available from Onyx now owned by Stepan Chemical Co. as Myristalkonium Chloride and Lonza Chemical Co. as BARQUAT TM.

The concentration of the sanitizing agent within the chemical sanitizer (40) of the present invention is dependent on a great number of factors including the intended environment of application, the quantity of drain flow over time, the temperature of the drain flow, the sanitizing agent or agents used within the chemical sanitizer (40), the hardness of the drain water, the physical size of the chemical sanitizer (40) once hardened, and the concentration of the other constituents, such as the hardeners used in the chemical sanitizer (40).

With these considerations in mind, the concentration of the sanitizing agent can vary broadly from about 5% to about 80% (w/w) of the chemical sanitizing agent. Given certain applications, the sanitizing agent may comprise 100% (w/w) of the chemical sanitizer (40) if the intended system requires a readily soluble sanitizing agent and a solid sanitizer such as, for example, a naphthylene substituted cationic is available for use. Practicalities such as the physical characteristics of the chemical sanitizer (40) including the rate of hardening and the expense of producing the drain sanitizing article (9) of the present invention most often dictate that the sanitizing agent be present in an intermediate concentration range from about 15% to 20% up to 70% (w/w) of the chemical sanitizer (40). Furthermore, the sanitizing agent is present in a preferred range of about 30% to 60% (w/w) of the chemical sanitizer (40) which provides the greatest formulatory ease for varying the concentrations of hardeners within the formulation.

The chemical sanitizer (40) used in the drain sanitizing article (9) may also comprise a hardener. The primary functions of the hardener are to promote a loss of malleability in the formed chemical sanitizer (40) and to control or modify the solubility of the sanitizing agent after it is poured into the cavity (15) of the housing (10). The nature of the chemical sanitizer of the present invention is such that more than one hardener may be used and, further, it is possible to use one constituent to impart hardness and another constituent to modify solubility. Accordingly, the hardener used should be capable of forming a homogeneous matrix with the sanitizing agent when mixed. Only with a homogeneous mixture of hardener and sanitizing agent will the chemical sanitizer (40) be able to provide a uniform dissolution when exposed to drainage. Moreover, given an intended use, the selected hardener by itself or in combination with an additional solubility modifying constituent should be able to promote varying degrees of aqueous solubility depending on the hardener chosen and the hardener concentration within the chemical sanitizer (40).

Generally, any agent or combination of agents which provides the requisite degree of hardness and aqueous solubility may be used if compatible with the sanitizing agent. However, if the drain sanitizing article (9) is to be used in a food process environment where there will be a high flow of heated drainage, the hardener should provide a relatively low degree of aqueous solubility to the chemical sanitizer (40). Such food processing environments are usually found in the critical filling and processing areas located within the food processing facilities. In contrast, if the intended food processing environment has a lower flow or cool water drainage, the hardener should provide for a higher degree of aqueous solubility allowing release of an effective amount of the sanitizing agent from the chemical sanitizer (40) of the present invention.

The hardener may be selected from any organic or inorganic compound which imparts a hardness and/or controls soluble character when placed in an aqueous environment. Compositions which can be used in the chemical sanitizer (40) of the present invention to vary hardness and solubility include amides such as stearic monoethanolamide, lauric diethanolamide, and stearic diethanolamide available from Stepan Chemical as NINOL TM amides, and Scher Chemical Company as SCHERCOMID TM amide products. Nonionic surfactants have also been found to impart varying degrees of hardness and solubility when combined with a coupler such as propylene glycol or polyethylene glycol commercially available from Union Carbide Corporation as CARBOWAX TM. Nonionics useful in this invention include nonyl phenol ethoxylates, linear alkyl alcohol ethoxylates, and ethylene oxide/propylene oxide block copolymers such as the PLURONIC TM surfactants commercially available from BASF Wyandotte. Nonionics particularly desirable as hardeners are those which are solid at room temperature and have an inherently reduced aqueous solubility as the result of combination with a coupling agent.

Other compositions which may be used as hardeners within the chemical sanitizer (40) of the present invention include urea also known as carbamide; starches which have been made water soluble through an acid or alkaline treatment processes including the acid processed amylose fraction of potato starch and various inorganics which either impart solidifying properties to a heated liquid matrix upon cooling or which can be pressed into tablets for carrying the sanitizing agent such as calcium carbonate, sodium sulfate and sodium bisulfate.

While the hardener used in the present invention can be any number of agents or combination of agents, amides and urea have been found to further the intended functions of the drain sanitizing article of the present invention. Specifically, alkyl amides provide formulation ease when combined with sanitizing agents, such as cationic surfactants, which allows for varied degrees of hardness and solubility and, in turn, versatile application to the many environments found in the food processing industry. Specifically, straight chain aliphatic alkyl amides provide a higher degree of insolubility with a corresponding higher degree of hardness. Generally, the alkyl chain of these amides ranges from $C_{16}$ to about $C_{18}$. Alkyl chains such as, for example, stearic chains when part of an amide hardener produce a hardened chemical sanitizer (40) where the sanitizing agent dissolves slowly as the hardener dissolves or disperses. Moreover, maintaining the amide as a mono-substituted amide, instead of a di-substituted amide, also ensures a high degree of insolubility and hardness.

In contrast, branched or di-substituted amides provide a higher degree of aqueous solubility with the lower degree of hardness and the resulting chemical sanitizer. It is thought that the degree of hardness in the resulting chemical sanitizer is related to the melting point of the amide constituent. Moreover, a di-substituted amide having an alkyl chain of about $C_{12}$ to $C_{14}$ such as, for example a lauryl chain, defines a chemical sanitizer (40) having greater aqueous solubility and a much more malleable character. Hardeners such as lauric diethanolamide offer a contrasting extreme to hardeners such as a stearic monoethanolamide, and are more applicable to low flow, cold runoff drain environments.

Another hardener and solubility modifier found to be useful in the chemical sanitizer (40) of the present invention is urea. The addition of urea to the chemical sanitizer (40) provides hardness without the usual decrease in aqueous solubility. As a result, urea can be used to provide a relatively high degree of aqueous solubility while maintaining a high degree of hardness. Such a chemical sanitizer (40) may be useful for areas which receive an inordinately low flow of drainage but yet have a persistently high degree of microbial and bacterial load.

The quantity of hardener used varies depending upon the same considerations which affected the quantity or concentration of the sanitizing agent. In fact, if a solid sanitizing agent is used such as a cationic surfactant like a naphthylene substituted quaternary ammonium chloride such as dimethyl 1-naphthyl methyl ammonium chloride available from Onyx Chemical Co. now owned by Stepan Chemical Company there may be no need at all to include a hardener.

However, a certain concentration of hardener is generally desirable within the chemical sanitizer (40) of the present invention for purposes of altering the solubility of the chemical sanitizer (40). Complimenting the broad general range of the sanitizing agent the hardener may be present at a level which varies from about 0% to about 95% (w/w) of a chemical sanitizer (40). Preferably, the hardener is present at a concentration of about 30% to 80% (w/w) and most preferably a concentration of about 40% to 70% (w/w) which provides the most versatility in the hardness and solubility of the chemical sanitizer (40).

When the drain sanitizing article (9), housing (10) is tinted or colored, it may be desirable to retain the natural opaque or light color of the chemical sanitizer (40) in order to provide a color contrast visually indicative of the continued presence of the chemical sanitizer (40) in the drain environment. However, the chemical sanitizer (40) of the present invention may also contain a dye. The dye functions in combination with the housing (10), when the housing (10) is clear or translucent, as an indicator. Primarily, this indicating function is brought forth first when the drain sanitizing article (9) is placed in the intended environment of use. Specifically, visual inspection of the color of the drain sanitizing article (9) prior to use denotes whether the specific drain sanitizing article (9) is appropriate for the intended use.

For instance, drain sanitizing article (9) which are to be used and drains receiving a lower temperature or flow of drainage may be dyed blue to represent a chemical sanitizer (40) having a high degree of solubility when exposed to a minimal drain flow or a drain flow of cooler temperature. Alternatively, the drain sanitizing article (9) may have a red color to indicate an intended use in drains receiving a higher flow of warmer drainage.

Once the drain sanitizing article (9) is placed within the intended environment of use the dye additionally functions to disclose the active presence of chemical sanitizer (40). This allows a visual determination of whether the chemical sanitizer (40) is still present in the housing (10) and, in turn, the drain sanitizing article (9) is still actively working. Often times, a drain cover may partially obscure the drain area and prevent easy visual inspection of a sanitizing article. A colored chemical sanitizer (40), in contrast to a sanitizing that is translucent provides the color contrast with the tinted housing (10) or drain environment (50) necessary to determine whether chemical sanitizer (40) is exhausted. Otherwise, an opaque or translucent color may preclude disclosure of the presence of the chemical sanitizer without removal of the obscuring drain cover.

Generally, the dye used in the chemical sanitizer (40) of the present invention must be temperature stable and oil soluble as the formulation process of the chemical sanitizer (40) tends to be free of aqueous constituents. Moreover, the dye must be compatible with the sanitizing agent and hardeners used in the chemical sanitizer (40). For instance, if a cationic surfactant is used as a sanitizing agent, the dye must be cationic or nonionic in order to avoid the complexing that would occur within an anionic dye.

Generally, any dye which satisfies the preceding requirements may be used in a chemical sanitizer of the present invention. Preferably, colorants such as 9,10-anthracenedione,1,4-bis[(alkyl phenyl) amino] and 9,10-anthracenedione,1, [(1-methylethyl) amino] commercially available from sources such as Morton Thiokol Corporation can be used within the chemical sanitizer (40) of the present invention.

The quantity of dye generally ranges from about 0% to 0.1% with a preferred range of about 0.01% to 0.05%. In actuality, the concentration of the dye depends upon the dye used, keeping in mind that the principle function of the dye is to provide an indicator not only of the type of chemical sanitizer (40) within the drain sanitizing article (9), but also to provide a contrast which is indicative of the presence of active sanitizing agent once the drain sanitizing article (9) is placed in use.

WORKING EXAMPLES

To mix the chemical sanitizer (40) of the present invention, the sanitizing agent is charged into a mixing tank and the tank is heated with appropriate agitation. This controlled agitation prevents the entrapment of air and, in turn, excessive foam in the mix. The hardening constituent, and optionally the dye, is then slowly metered in to the sanitizing agent with continued agitation. The mixture is then heated and agitated until the hardening constituent is melted or dissolved. The formulation, now the complete chemical sanitizing agent is decanted into individual housings.

The invention will now be illustrated through a number of working examples concerning the formulation and the microbial efficacy of the drain sanitizing article of the present invention.

TABLE I

| Formulatory Working Examples (Concentration in wt-%) | | | |
| --- | --- | --- | --- |
| | EXAMPLE | | |
| | 1 | 2 | 3 |
| HARDENERS | 25 | 90 | 10 |
| Stearic Monoethanolamide | | | 80 |
| Stearic Diethanolamide | | | |
| Lauric Diethanolamide | | | |
| Urea | | | |

TABLE I-continued
Formulatory Working Examples
(Concentration in wt-%)

| | Example 1 | Example 2 | Example 3 | Example 4 | Example 5 | Example 6 | Example 7 | Example 8 | Example 9 | Example 10 | Example 11 | Example 12 | Example 13 | Example 14 | Example 15 | Example 16 | Example 17 |
|---|---|---|---|---|---|---|---|---|---|---|---|---|---|---|---|---|---|
| HARDENERS | | | | | | | | | | | | | | | | | |
| Stearic Monoethanolamide | | | | 30 | | | 20 | 25 | | 20 | 10 | 10 | | 20 | 30 | 44.98 | 12.00 |
| Stearic Diethanolamide | | | | | | | | | | 20 | 40 | | | | | | 23.98 |
| Lauric Diethanolamide | | | | 20 | | | | | | | | 40 | | | | | |
| Urea | | | | | 50 | | 20 | | 25 | | | | | | | | 22.00 |
| Butoxypolypropoxylenoxy polyethylenoxyethanol | | | | | | | | 25 | 25 | | | | | | | | |
| (C12-15) Alcohol (Et-O)12 Ethoxylate | | | | | | | 20 | | | | | | | | | | |
| Polyethylene glycol | | | | | 85 | | | | | | | | | | | | |
| CaCO3 | | | | | | | | | | | | | | 55 | | | |
| Starch | | | | | | | | | | | | | | | 20 | | |
| SANITIZERS | | | | | | | | | | | | | | | | | |
| n-Alkyl (C14-18) Dimethyl Benzyl Ammonium Chloride) | 75 | 10 | 10 | 50 | 50 | | | | | 60 | | | | 25 | 50 | 55.00 | 42.00 |
| n-Tetradecyl Dimethyl Benzyl Ammonium Chloride Monohydrate | | | | | | 15 | 40 | 50 | 50 | | | | | | | | |
| n-Alkyl (C12) Dimethyl 1-Naphthyl Methyl Ammonium Chloride | | | | | | | | | | | 50 | 50 | 100 | | | | |
| DYES | | | | | | | | | | | | | | | | | |
| 9,10-Anthracenedione, 1,4-bis[(alkylphenyl)amino] | | | | | | | | | | | | | | | | | |
| 9,10-Anthracenedione, 1-[(1-methylethyl)amino] | | | | | | | | | | | | | | | | | |
| RELATIVE HARDNESS | 1 | 3 | 2 | 2 | 3 | 1 | 2 | 1 | 3 | 3 | 2 | 1 | 3 | 3 | 3 | | |
| RELATIVE DISSOLVING RATE | 2 | 4 | 2 | 2 | 1 | 2 | 2 | 2 | 1 | 2 | 3 | 2 | 4 | 2 | 3 | | |

TABLE I-continued

Formulatory Working Examples
(Concentration in wt-%)

| DYES | | |
|---|---|---|
| 9,10-Anthracenedione, 1,4-bis[(alkylphenyl)amino] | | 0.02 |
| 9,10-Anthracenedione, 1-[(1-methylethyl)amino] | 0.02 | |
| RELATIVE HARDNESS | 3 | 1 |
| RELATIVE DISSOLVING RATE | 3 | 2 |

The relative hardness of the chemical sanitizing agent of the present invention in each of the examples, 1 through 17, was evaluated on a scale of 1 to 3. A relative hardness value of 3 indicates that the chemical sanitizing agent once in solid form could not be compressed by manual pressure. A relative hardness value of 2 indicates that the chemical sanitizing agent was compressible with the manual application of pressure. Finally, a relative hardness value of 1 indicates that the chemical sanitizing agent of the present invention was freely compressible by manual pressure.

The relative dissolving rate at room temperature of each of the Examples 1-17 is also indicated by the preceding table. A relatively fast dissolving rate is indicated by a valuation of 1 with a relatively slow dissolving rate being represented by a valuation of 4. Intermediate valuations of 2 and 3 represent moderately fast and moderately slow relative dissolving rates, respectively.

Bacteriocidal Efficacy

To illustrate typical bacteriocidal efficacy, Working Examples 16 and 17 were then tested. The bacteriocidal analysis was completed with accordance with AOAC Official Method of Analysis for Germicidal and Detergent Sanitizing Action of Disinfectants, §§4.020-4.029.

In accordance with the testing protocol defined by the AOAC, an analysis of the microbiological efficacy of Examples 16 and 17 was run to consider the microbiological activity of the drain sanitizing article of the present invention against colony forming units of *Staphylococcus aureus* (*S. aureus*) and *Escherichia coli* (*E. coli*). While drain treatment chemicals used need only exhibit a 3 log reduction (or 99.9%) in bacteria to be considered sanitizing, the present analysis was undertaken at the 5 log reduction (or 99.999%) level to show the bacteriocidal efficacy of the composition of the present invention. Initially, the control concentration of *E. coli* was $5.9 \times 10^7$ CFU/ml and the control concentration of *S. aureus* was $1.0 \times 10^7$ CFU/ml (CFU means Colony Forming Units). Test solutions of Examples 16 and 17 were made up from the chemical sanitizer (40) of each of examples 16 and 17 to provide solutions having 100 p.p.m. and 200 p.p.m. of sanitizing agent. The test solutions were then inoculated into colonies in accordance with AOAC testing procedures having the initial CFU/ml concentration shown in Table II, below.

Bacteriocidal testing was then completed on *E. coli* and *S. aureus* culture suspensions to determine the bacteriocidal efficacy of Working Examples 16 and 17. Detailed below are the two examples including the amount of reduction shown in percentage of reduction for each solution.

TABLE II

MICROBIOLOGICAL EFFICACY

| PRO-DUCT | P.P.M. QUAT | P.P.M. PRO-DUCT | INITIAL CFU/ml | RE-COVERED #CFU/ml | % RE-DUCTION |
|---|---|---|---|---|---|
| *E. Coli* | | | | | |
| Ex. 16 | 100 | 2020 | $5.9 \times 10^7$ | <10 | 99.999% |
|  | 200 | 4040 | $5.9 \times 10^7$ | <10 | 99.999% |
| Ex. 17 | 100 | 2646 | $5.9 \times 10^7$ | <10 | 99.999% |
|  | 200 | 5292 | $5.9 \times 10^7$ | <10 | 99.999% |
| *S. aureus* | | | | | |
| Ex. 16 | 100 | 2020 | $1.0 \times 10^7$ | <10 | 99.999% |
|  | 200 | 4040 | $1.0 \times 10^7$ | $2.0 \times 10^1$ | 99.999% |
| Ex. 17 | 100 | 2646 | $1.0 \times 10^7$ | $3.6 \times 10^2$ | 99.996% |
|  | 200 | 5292 | $1.0 \times 10^7$ | $1.0 \times 10^1$ | 99.999% |

EXAMPLE 18

To mix the chemical sanitizer (40) of the present invention, sodium 1-octane sulfonate (40% w/w) was charged into a mixing tank to the quantity of 19 wt. % of the entire mix. The tank was then heated with the appropriate agitation. Decanoic acid was then added to the mix at a weight of 10 wt. % of the mix followed by the addition of 60 wt. % powdered sodium bisulfate and 11 wt. % of powdered sodium 1-octane sulfonate to the mix with adequate agitation. The mixture was then heated and agitated until the constituents formed a homogeneous composition. The formulation was then decanted into individual housings.

Using the AOAC Official Method of Analysis for Germicidal and Detergent Sanitizing Action of Disinfectants, commonly known as the A.O.A.C. use dilution test, a bacterial analysis of Example 18 was completed. The analysis showed that given an initial concentration of $6.9 \times 10^7$ CFU/ml of *E. coli*, test solution of 50, 75, and 100 p.p.m. of decanoic acid equivalence in solution provided less than 10 CFU/ml in the final count or a 99.999% reduction in the count of bacteria cultures per ml.

EXAMPLE 19

Charge 34.5% phosphoric acid (85.0 w/w) into the mixing tank, heat and agitate at the appropriate rate. Slowly charge 47.8 wt. % urea into the mix, with continued agitation and heating while not exceeding 170° C. Charge 10.0 wt. % of polyoxypropylene-polyoxyethylene (m.w. 5600) and 0.20 wt. % of coconut fatty acid (m.w. 198) into the mix and cool the formulation to 125° C. A premix which is 7.50 wt. % of the total formulation (the premix comprises 4.43 wt. % $I_2$, 1.95 wt. % NaI and 1.12 wt. % of deionized water of the total formulation) was then charged into the mix. The mixture was then agitated at 125° C. until all the constituents were melted or dissolved. The complete formulation was then decanted into individual housings.

A bacterial analysis of the resulting product in accordance with AOAC Testing Protocol for Available Chlorine Germicidal Equivalent Concentration (Official Final Action, A.O.A.C. Methods of Analysis, 14th edition, 1984) was then run to determine the efficacy of the resulting product. It was determined that a quantity of product equivalent to provide 12.5 p.p.m. of titratable $I_2$ was equivalent to 100 p.p.m. of available chlorine in bacteriocidal efficacy. Moreover, it was determined that a quantity of product equivalent to provide 25.0 p.p.m. titratable $I_2$ was equivalent to provide 200 p.p.m. available chlorine in bacteriocidal efficacy.

EXAMPLE 20

To mix the chemical sanitizer (40) of the present invention, the hardening constituent in the form of 45 wt. % of stearic monoethanolamide is charged into the tank and the tank is heated with appropriate agitation. The sanitizing agent in the form of 35 wt. % of dodecyl benzene sulfonic acid sodium salt is then charged into a mixing tank with continued heating and appropriate agitation. Finally, 20 wt. % of powdered sodium bisulfate is added to the formulation. The mixture is then heated and agitated until all the constituents are melted or dissolved. The then completed chemical sanitizing agent is then decanted into individual housings.

EXAMPLE 21

To mix the chemical sanitizer (40) of the present invention, the hardening constituent, in the form of 45 wt. % of stearic monoethanolamide and 10 wt. % of stearic diethanolamide are charged into the tank and heated with appropriate agitation. The sanitizing agent in the form of 45 wt. % of o-phenyl phenol sodium salt is charged into a mixing tank with continued heating and agitation. The mixture is then heated and agitated until the hardening constituents, as well as the sanitizing agent, is melted or dissolved. The formulation, now the complete sanitizing agent, is then decanted into individual housings.

EXAMPLE 22

To mix the chemical sanitizer (40) of the present invention, the hardening constituent, in the form of 50 wt. % of stearic monoethanolamide and 10 wt. % of stearic diethanolamide is slowly metered into the mixing tank and the tank is heated with appropriate agitation. The chemical sanitizing agent in the form encapsulated sodium dichloro-s-triazinetrione dihydrate (as disclosed in U.S. Pat. Nos. 4,731,195; 4,681,914; and 4,657,784 which are incorporated herein by reference) is charged into the mixing tank with continued heating and agitation. The mixture is then heated and agitated until the hardening constituent is melted. The formulation, now the complete sanitizing agent, is decanted into individual housings.

We claim:

1. A drain sanitizing article for dispensing a chemical sanitizing agent for sanitizing running and standing drainage said drain sanitizing article comprising a housing, said housing having an inner wall, defining an opening in said housing for the passage of drainage over the article into the drain, and a bottom wall, said bottom wall cooperatively connected to said inner wall and forming a cavity in said housing, and a hardened aqueous soluble chemical sanitizing agent contained within the cavity of said housing, said sanitizing agent comprising (a) an effective amount of an antimicrobial sanitizer, and (b) an effective amount of hardener.

2. The article of claim 1 additionally comprising an effective amount of a solubility modifier.

3. The article of claim 1 additionally comprising an effective amount of dye wherein said dye indicates the intended environment of use of the chemical sanitizing agent and the continued presence of the chemical sanitizing agent once installed.

4. The article of claim 1 wherein said chemical sanitizing agent is a hardened pressed tablet.

5. The article of claim 1 wherein said antimicrobial sanitizer comprises an n-alkyl dimethyl benzyl ammonium chloride.

6. The article of claim 5 wherein said n-alkyl dimethyl benzyl ammonium chloride is selected from the group consisting of n-tetradecyl n-alkyl dimethyl benzyl ammonium chloride monohydrate, n-alkyl dimethyl benzyl 1-naphthylmethyl ammonium chloride, and mixtures thereof.

7. The article of claim 1 wherein the antimicrobial sanitizer comprises an organic encapsulated chlorine donating agent selected from the group consisting of trichloro(iso)cyanuric acid, sodium dichloro(sio)cyanurate potassium dichloro(iso)cyanurate, sodium dichloro(sio)cyanuarate dihydrate, and mixtures thereof, said chorine donating agent being present in the concentration of about 5 wt. % to 80 wt. %.

8. The article of claim 1 wherein said antimicrobial sanitizer comprises an inorganic chlorine source selected from the group consisting of LiOCl, Ca(OCl)$_2$, and mixtures thereof.

9. The article of claim 1 wherein said antimicrobial sanitizer comprises a phenol source selected from the group consisting of o-phenylphenol, 2,4,5-trichlorophenol, 2,4,6-trichlorophenol, 2-chloro-4-phenylphenol, 2,3,4,6-tetrachlorophenol, pentachlorophenol, 4-chloro-2-phenylphenol, 6-chloro-2-phenylphenol, Na-o-phenylphenol, Na-2,4,5-trichlorophenol, Na-pentachlorophenol, and mixtures thereof, said phenol source being present in a concentration of about 5 wt. % to 80 wt. %.

10. The article of claim 1 wherein said antimicrobial sanitizer comprises an aldehyde selected from a group consisting of formaldehyde, glutaraldehyde, and mixtures thereof, said aldehyde being present in the concentration of about 5 wt. % to 80 wt. %.

11. The article of claim 1 where said antimicrobial sanitizer comprises an iodophor selected from the group consisting of iodine-nonionic surfactant complexes, iodine-polyvinyl pyrollidone complexes, iodine-quaternary ammonium chloride complexes, amphoteric-iodine complexes, and mixtures thereof, said iodophor being present at a concentration of about 5 wt. % to 80 wt. %.

12. The article of claim 1 wherein said hardener comprises an alkyl amide selected from the group consisting of lauric diethanolamide, stearic diethanolamide, stearic monoethanolamide, and mixtures thereof, said alkylamides being present at a concentration of from about 20 wt. % to 95 wt. %.

13. The article of claim 1 wherein said hardener comprises a nonionic surfactant selected from the group consisting of nonyl phenol ethoxylates, C$_{12-14}$ linear alcohol ethoxylates, ethylene oxide/propylene oxide copolymers, and mixtures thereof, said nonionic surfactants being present at a concentration of from about 20 wt. % to 95 wt. %.

14. The article of claim 13 wherein said hardener additionally comprises a coupling agent, said coupling agent selected from the group consisting of propylene glycol, polyethylene glycol, and mixtures thereof, said coupling agent being present at a concentration of from about 20 wt. % to 95 wt. %.

15. The article of claim 1 wherein said hardener comprises a water soluble starch present at a concentration of from about 20 wt. % to 95 wt. %.

16. The article of claim 1 wherein said hardener comprises urea present at a concentration of from about 20 wt. % to 95 wt. %.

17. The article of claim 1 additionally comprising a solubility modifier.

18. The article of claim 5 wherein said antimicrobial sanitizer comprises an n-alkyl dimethyl benzyl ammonium chloride, the alkyl group comprising 60 wt. % $C_{14}$, 30 wt. %, 5 wt. % $C_{12}$, and 5 wt. % $C_{18}$.

19. The article of claim 1 wherein said antimicrobial sanitizer comprises a quaternary alkyl dimethyl benzyl ammonium chloride present in a concentration ranging from about 30 wt. % to 60 wt. % and a hardener comprising an alkyl mono ethanolamide present in a concentration ranging from about 30 wt. % to 80 wt. %.

20. The drain sanitizing article of claim 1 additionally comprising means for destructibly removing a portion of said housing, said destructible removing means patterned into said housing wherein tearing said destructible removing means affects removal of a portion of said housing thereby exposing said chemical sanitizing agent.

21. The drain sanitizing article of claim 1 wherein said housing additionally comprises a handle cooperatively connected to said housing inner wall and spanning the opening of said housing.

22. The drain sanitizing article of claim 1 wherein said housing additionally comprises a housing outer wall affixed to said housing bottom wall and a handle cooperatively connected to said housing outer wall and spanning the opening of said housing.

23. The drain sanitizing article of claim 1 wherein said housing additionally comprises a handle cooperatively connected to said housing inner wall and spanning the opening of said housing.

24. The drain sanitizing article of claim 1 wherein said housing is of one piece molded construction.

25. The drain sanitizing article of claim 20 wherein said housing, and said removing means are of one piece molded construction.

26. The drain sanitizing article of claims 22 or 23 wherein said housing, and said handle are of one piece molded construction.

27. The drain sanitizing article of claim 26 wherein said housing, removing means, and said handle are of one piece molded construction.

28. The drain sanitizing article of claim 27 wherein said one piece molded housing, removing means and handle comprises a polymeric material selected from the group consisting of polypropylene, polyethylene, and mixtures thereof.

29. An article for dispensing a chemical sanitizing agent for sanitizing running and standing drainage said drain sanitizing article comprising a housing, said housing having an inner wall defining an opening in said housing for the passage of drainage over the article into the drain, an outer wall, and a bottom wall, said bottom wall cooperatively connecting said inner and outer walls and forming an inner cavity in said housing for containing a chemical sanitizing agent, said chemical sanitizing agent contained within said housing inner cavity and comprising (a) an effective amount of an antimicrobial sanitizer, and (b) an effective amount of hardener, said article further comprising means for destructibly removing a portion of said housing, said destructible removing means patterned into said housing wherein tearing said destructible removing means affects removal of a portion of said housing thereby exposing said chemical sanitizing agent.

30. The article of claim 29 additionally comprising an effective amount of a solubility modifier.

31. The article of claim 29 additionally comprising an effective amount of dye wherein said dye indicates the intended environment of use of the chemical sanitizing agent and the continued presence of the chemical sanitizing agent once installed.

32. The article of claim 29 wherein said chemical sanitizing agent is a hardened pressed tablet.

33. The article of claim 29 wherein said antimicrobial sanitizer comprises an n-alkyl dimethyl benzyl ammonium chloride.

34. The article of claim 33 wherein said n-alkyl dimethyl benzyl ammonium chloride is selected from the group consisting of n-tetradecyl n-alkyl dimethyl benzyl ammonium chloride monohydrate, n-alkyl dimethyl benzyl 1-naphthylmethyl ammonium chloride and mixtures thereof.

35. The article of claim 29 wherein the antimicrobial sanitizer comprises an organic encapsulated chlorine denoting agent selected from the group consisting of trichloro(sio)cyanuric acid, sodium dichloro(iso)cyanurate potassium dichloro(iso)cyanurate, sodium dichloro(iso)cyanurate dihydrate, and mixtures thereof, said chorine donating agent being present in the concentration of about 5 wt. % to 80 wt. %.

36. The article of claim 29 wherein said antimicrobial sanitizer comprises an inorganic chlorine source selected from the group consisting of LiOCl, $Ca(OCl)_2$, and mixtures thereof.

37. The article of claim 29 wherein said antimicrobial sanitizer comprises a phenol source selected from the group consisting of o-phenylphenol, 2,4,5-trichlorophenol, 2,4,6-trichlorophenol, 2-chloro-4-phenylphenol, 2,3,4,6-tetrachlorophenol, pentachlorphenol, 4-chloro-2-phenylphenol, 6-cloro-2-phenylphenol, Na-o-phenylphenol, Na-2,4,5-trichlorophenol, Na-pentachlorophenol, and mixtures thereof, said phenol source being present in a concentration of about 5 wt. % to 80 wt. %.

38. The article of claim 29 wherein said antimicrobial sanitizer comprises an aldehyde selected from a group consisting of formaldehyde, glutaraldehyde, and mixtures thereof, said aldehyde being present in the concentration of about 5 wt. % to 80 wt. %.

39. The article of claim 29 wherein said antimicrobial sanitizer comprises an iodophor selected from the group consisting of iodine-nonionic surfactant complexes, iodine-polyvinyl pyrollidone complexes, iodine-quarternary ammonium chloride complexes, amphoteric-iodine complexes, and mixtures thereof, said iodophor being present at a concentration of about 5 wt. % to 80 wt. %.

40. The article of claim 29 wherein said hardener comprises an alkyl amide selected from the group consisting of lauric diethanolamide, stearic diethanolamide, stearic monoethanolamide, and mixtures thereof, said alkylamides being present at a concentration of from about 20 wt. % to 95 wt. %.

41. The article of claim 29 wherein said hardener comprises a nonionic surfactant selected from the group consisting of nonyl phenol ethoxylates, $C_{12-14}$ linear alcohol ethoxylates, ethylene oxide/propylene oxide copolymers, and mixtures thereof, said nonionic surfactants being present at a concentration of from about 20 wt. % to 95 wt. %.

42. The article of claim 41 wherein said hardener additionally comprises a coupling agent, said coupling agent selected from the group consisting of propylene glycol, polyethylene glycol, and mixtures thereof, said coupling agent being present at a concentration of from about 20 wt. % to 95 wt. %.

43. The article of claim 29 wherein said hardener comprises a water soluble starch present at a concentration of from about 20 wt. % to 95 wt. %.

44. The article of claim 29 wherein said hardener comprises urea present at a concentration of from about 20 wt. % to 95 wt. %.

45. The article of claim 29 additionally comprising a solubility modifier.

46. The article of claim 29 wherein said antimicrobial sanitizer comprises an n-alkyl dimethyl benzyl ammonium chloride, the alkyl group comprising 60 wt. % $C_{14}$, 30 wt. % $C_{16}$, 5 wt. % $C_{12}$, and 5 wt. % $C_{18}$.

47. The article of claim 29 wherein said antimicrobial sanitizer comprises a quaternary alkyl dimethyl benzyl ammonium chloride present in a concentration ranging from about 30 wt. % to 60 wt. % and a hardener comprising an alkyl mono ethanolamide present in a concentration ranging from about 30 wt. % to 80 wt. %.

48. A drain sanitizing article for dispensing a chemical sanitizing agent for sanitizing running and standing drainage, said sanitizing article comprising a removable housing comprising an inner wall defining a central opening, said inner wall forming a cavity, said article further comprising a hardened aqueous soluble chemical sanitizing agent contained within the cavity of said housing, said sanitizing agent comprising from about 30 wt. % to 60 wt. % of a quaternary alkyl dimethyl benzyl ammonium chloride and about 30 wt. % to 80 wt. % of an alkyl mono ethanolamide.

49. The drain sanitizing article of claim 29 wherein said housing additionally comprises a handle cooperatively connected to said housing inner wall and spanning the opening of said housing.

50. The drain sanitizing article of claim 29 wherein said housing additionally comprises a handle cooperatively connected to said housing outer wall and spanning the opening of said housing.

51. The drain sanitizing article of claim 29 wherein said housing comprises removing means, wherein said housing and said removing means are of one piece molded construction.

52. The drain sanitizing article of claim 29 wherein said housing comprises a polymeric material selected from the group consisting of polypropylene, polyethylene, and mixtures thereof.

* * * * *

UNITED STATES PATENT AND TRADEMARK OFFICE
CERTIFICATE OF CORRECTION

PATENT NO. : 5,312,624  Page 1 of 3
DATED : May 17, 1994
INVENTOR(S) : Francis L. Richter et al.

It is certified that error appears in the above-identified patent and that said Letters Patent is hereby corrected as shown below:

On column 1, line 37, please delete "tychimurium" and substitute therefore --typhimurium--

On column 4, line 52, please delete "a" after the word "providing"

On column 4, line 53, please insert --of-- after the word "removal"

On column 5, line 2, please insert --be-- after the word "to"

On column 11, line 32, please delete "Complimenting" and substitute therefore --Complementing--

On column 18, line 15 (claim 7), please delete "cyanurarate" and substitute therefore --cyanurate--

On column 18, line 33 (claim 10), please delete "a" and substitute therefore --the--

On column 19, line 6 (claim 18), please insert --$C_{16}$-- after the word "30wt.%"

On column 20, line 19 (claim 35), please delete "denoting" and substitute therefore --donating--

On column 20, line 20 (claim 35), please delete "(sio)" and substitute therefore --(iso)--

UNITED STATES PATENT AND TRADEMARK OFFICE
CERTIFICATE OF CORRECTION

PATENT NO. : 5,312,624
DATED : May 17, 1994
INVENTOR(S) : Francis L. Richter et al.

It is certified that error appears in the above-identified patent and that said Letters Patent is hereby corrected as shown below:

On column 20, line 34 (claim 37), please delete "pentachlorphenol" and substitute therefore --pentachlorophenol--

On column 13, line 47, "20" and "25" should be on line 48

On column 13, line 52, "25" and "25" should be on line 53

On column 13, line 59, "40", "50" and "50" should be on line 60

On column 14, line 18, "60" should be on line 19

On column 14, line 20, "50" and "50" should be on line 21

On column 14, line 44, "100" should be on line 45

On column 14, line 64, "55.00" and "42.00" should be on line 65

On column 15, line 6, "0.02" should be on line 7

UNITED STATES PATENT AND TRADEMARK OFFICE
CERTIFICATE OF CORRECTION

Page 3 of 3

PATENT NO. : 5,312,624
DATED : May 17, 1994
INVENTOR(S) : Francis L. Richter, et. al.

It is certified that error appears in the above-indentified patent and that said Letters Patent is hereby corrected as shown below:

On column 15, line 8, "0.02" should be on line 9
On column 14, line 17, "Benzyl Ammonium Chloride)" should read--n-Tetradecyl Dimethyl Benzyl--; line 18, "n-Tetradecyl Dimethyl Benzyl" should read --Ammonium Chloride Monohydrate--; and line 65, Benzyl Ammonium Chloride)" should read --Ammonium Chloride--.

Signed and Sealed this

Twentieth Day of September, 1994

Attest:

BRUCE LEHMAN

*Attesting Officer*        *Commissioner of Patents and Trademarks*